(12) United States Patent
Derzon

(10) Patent No.: US 12,298,188 B2
(45) Date of Patent: May 13, 2025

(54) RADIATION POWERED HIGH DOSE RATE AND HIGH DOSE RADIATION SENSOR

(71) Applicant: Gold Standard Radiation Detection Inc., Albuquerque, NM (US)

(72) Inventor: Mark Derzon, Albuquerque, NM (US)

(73) Assignee: Gold Standard Radiation Detection, Inc., Albuquerque, NM (US)

(*) Notice: Subject to any disclaimer, the term of this patent is extended or adjusted under 35 U.S.C. 154(b) by 707 days.

(21) Appl. No.: 17/292,353

(22) PCT Filed: Nov. 21, 2019

(86) PCT No.: PCT/US2019/062698
§ 371 (c)(1),
(2) Date: May 7, 2021

(87) PCT Pub. No.: WO2020/107004
PCT Pub. Date: May 28, 2020

(65) Prior Publication Data
US 2022/0003609 A1    Jan. 6, 2022

Related U.S. Application Data

(60) Provisional application No. 62/770,383, filed on Nov. 21, 2018.

(51) Int. Cl.
*H01L 35/16* (2006.01)
*G01J 5/06* (2022.01)
(Continued)

(52) U.S. Cl.
CPC . *G01J 5/16* (2013.01); *G01J 5/06* (2013.01); *H10N 10/17* (2023.02);
(Continued)

(58) Field of Classification Search
None
See application file for complete search history.

(56) References Cited

U.S. PATENT DOCUMENTS 5,056,929 A * 10/1991 Watanabe ............... G01J 5/12
374/129
5,695,283 A * 12/1997 Johnson .................. G01J 5/16
136/208
(Continued)

FOREIGN PATENT DOCUMENTS

KR    20150114347 A    10/2015
WO    WO-2020107004 A1    5/2020

OTHER PUBLICATIONS

Extended European Search Report for European Application No. 19888229.2, dated Jul. 4, 2022, 7 pages.
(Continued)

*Primary Examiner* — Hoon K Song
(74) *Attorney, Agent, or Firm* — COOLEY LLP (57) ABSTRACT

The present invention provides apparatuses comprising a plurality of junctions providing a Seebeck effect, configured as alternating hot and cold junctions. The apparatus can be configured such that the cold junctions exhibit a different thermal behavior than the hot junctions in response to incident radiation. The junctions can be connected in series, such that the sum of the Seebeck effect from the plurality of junctions provides a sensitive, inherently calibrated indication of heating of the apparatus responsive to incident radiation, and therefore of the radiation itself.

20 Claims, 7 Drawing Sheets

(51) Int. Cl.
*G01J 5/16* (2006.01)
*H10N 10/17* (2023.01)
*H10N 10/851* (2023.01)
*H10N 10/852* (2023.01)
*H10N 10/853* (2023.01)
*A61B 6/10* (2006.01)
*A61B 6/42* (2024.01)

(52) U.S. Cl.
CPC ......... *H10N 10/852* (2023.02); *H10N 10/853* (2023.02); *H10N 10/8556* (2023.02); *A61B 6/107* (2013.01); *A61B 6/4208* (2013.01); *G01J 2005/065* (2013.01)

(56) References Cited

U.S. PATENT DOCUMENTS

| | | | | |
|---|---|---|---|---|
| 6,509,520 | B1 | 1/2003 | Kyle | |
| 6,670,538 | B2* | 12/2003 | Wilner | G01K 17/003 257/E31.093 |
| 7,884,277 | B2* | 2/2011 | Perlo | H10N 10/13 136/201 |
| 8,304,851 | B2* | 11/2012 | Trifonov | H10N 19/00 257/470 |
| 9,267,847 | B2* | 2/2016 | Kassovski | G01J 5/12 |
| 2008/0017236 | A1* | 1/2008 | Perlo | H10N 10/13 136/201 |
| 2009/0025774 | A1* | 1/2009 | Plissonnier | H10N 10/17 136/238 |
| 2014/0284480 | A1* | 9/2014 | Yonemura | G01J 5/046 250/338.1 |
| 2018/0231420 | A1* | 8/2018 | Saitou | G01J 5/12 |
| 2020/0028055 | A1* | 1/2020 | Shibata | H10N 10/17 |

OTHER PUBLICATIONS

International Preliminary Report on Patentability for International Application No. PCT/US2019/062698, dated May 21, 2021, 9 pages.

International Search Report and Written Opinion of the International Searching Authority for International Application No. PCT/US2019/062698, dated Mar. 2, 2020, 10 pages.

\* cited by examiner

FIG. 1

| Metals | Seebeck Coefficient |
|---|---|
|  | pV/K |
| Antimony | 47 |
| Nichrome | 25 |
| Molybdenum | 10 |
| Cadmium | 7.5 |
| Tungsten | 7.5 |
| Gold | 6.5 |
| Silver | 6.5 |
| Copper | 6.5 |
| Rhodium | 6.0 |
| Tantalum | 4.5 |
| Lead | 4.0 |
| Aluminum | 3.5 |
| Carbon | 3.0 |
| Mercury | 0.6 |
| Platinum | 0 |
| Sodium | -2.0 |
| Potassium | -9.0 |
| Nickel | -15 |
| Constantan | -35 |
| Bismuth | -72 |

| Semiconductors | Seebeck Coefficient |
|---|---|
|  | pV/K |
| Se | 900 |
| Te | 500 |
| Si | 440 |
| Ge | 300 |
| n-type $Bi_2Te_3$ | -230 |
| p-type $Bia.«SbJe_3$ | 300 |
| p-type $Sb_2Te_3$ | 185 |
| PbTe | -180 |
| PboaGe^Set,!? | 1670 |
| Pboe Ge3o Sese | 1410 |
| $Ge_{33}$ Sesa | -1360 |
| Pbi 3 G©2O Se 58 | -1710 |
| Pbi5Ge37 Se&8 | -1990 |
| SnSbaTe7 | 25 |
| SnBuTe7 | 120 |
| SnBbSbJe7 | 151 |
| SnBbsSbi sTer | 110 |
| $SnBi_2 Sb_2Te7$ | 90 |
| $PbBi_4Te7$ | -53 |

FIG. 2

| Event | Dose (rad) | Doserate (rad/s) | Impulse Voltage From a Single Junction (V) | Impulse from a 10,000 Junction Array (V) |
|---|---|---|---|---|
| Background | 0.6 in year | 2e-8 | 4e-20 | 4e-16 |
| Cat Scan | ~0.1-0.3 in 10 min | >3e-4 | >7e-16 | >7e-12 |
| Routine x ray | 0.01 in 1 us | 1e4 | 2e-8 | 2e-4 |
| Gamma Knife procedure | 400 in 10 min to 1hr | ~1 | ~2e-12 | 2e-8 |
| Nuclear Event | >>600 in 1 s | >>600 | >>1.2e-3 | >>12 |

Ring Embodiment, 91

RADIATION POWERED HIGH DOSE RATE AND HIGH DOSE RADIATION SENSOR

Cross-reference to Related Applications

This application is a national stage application under 35 U.S.C. 371 of PCT application PCT/US19/62698, filed 11 Nov. 2019, which claims priority to U.S. provisional application 62770383 filed 21 Nov. 2018. Each of the foregoing is incorporated by reference herein.

TECHNICAL FIELD

This invention is in the field of radiation sensors, specifically in the field of measurement of radiation dose and dose rate.

BACKGROUND ART

Radiation is measured and inferred in many ways. Radiation dose is the most common way to reference biological damage. It is rarely measured directly—it is inferred from some other measurement or processing of some other measurement. The definition of radiation dose is in energy deposited per unit mass (ergs per gram). The present invention can directly measure ergs/g.

Many of the sensors available today use large bulk sensors such as scintillators or semiconductors or other methods to infer radiation dose. All of these, where the ergs/gram are not measured directly, can engender uncertainties because the ionizing particle interactions need to be known well to estimate the dose (ergs/g) from the flux, light or charge produced. Those uncertainties are typically 5 percent or greater. This is because the basic cross sections or interaction probabilities are rarely known to better than 5%; you cannot calculate an inferred dose or energy deposition which involve many of these interactions with an uncertainty better than the basic physical interactions and derive a dose number that is better known than the inputs.

The implications in the medical community is important. For instance, in The Int. Journal of Radiation Oncology, Jul. 15, 1995, Volume 32, Issue 4, Pages 1227-1237 the importance of being within 1% emphasized. It can mean the difference between life and death.

Therefore, there are important medical and industrial needs for sensors with very low uncertainty in dose. In order to attain this low uncertainty with conventional sensors, the temperature rise from irradiation must be measured. No one commercially or commonly measures radiation dose directly. This is because the temperature rise is much lower (read 10,000 to 1 million times smaller) than environmental temperature change in many situations. This invention changes that for many practical situations.

In addition to providing indirect measurement of dose and dose rate, most radiation sensors require power during the sensing process. For example, this means a voltage bias is required to a phototube or across a semiconductor to sweep a charge. The method described here requires no power to the sensing element.

Penetrating and ionizing radiation sensors are commonly scintillation based (light emission), or charge collection based (gas detectors such as the Geiger Mueller tube, proportional counters, or semiconductors). These are relatively sensitive and require active electronics to power the transducer element (e.g. phototube).

For infrared (IR) or thermal forms of radiation, pyroelectric or thermocouple devices can be used. More sensitive thermal devices such as thermistors or resistive temperature sensors have some sort of imposed bias—necessitating a power source, which is always on and requiring power when there is no appreciable radiation. This means an electric field source is applied and the change in resistance is measured electronically.

For the pyroelectric or resistive devices power is required for the entire time the device is used, and calibration and reproducibility can be problematic. A complex process must be used to calibrate the device, particularly for the low temperature changes expected with penetrating radiation as the means of measuring dose. and complex calibration. Complex analog and digital circuitry is often required to obtain full time-dependent measurements of the integral dose.

The manufacture of the element determines the specific current (or voltage change) when exposed to the radiation. These are not typically used for ionizing radiation or penetrating radiation such as gammas or neutrons.

DISCLOSURE OF INVENTION

Embodiments of the present invention provide an apparatus for the measurement of radiation, comprising: (a) a first plurality of elements comprising a first material; (b) a second plurality of elements comprising a second material; (c) wherein the first plurality of elements and second plurality of elements are configured to form a third plurality of junctions and fourth plurality of junctions, connected in series comprising alternating junctions from the third and fourth plurality of junctions; with the first junction in the series in electrical communication with a first electrode, and the last junction in the series in electrical communication with a second electrode; and (d) wherein junctions in the third plurality have a different thermal response to incident radiation that junctions in the fourth plurality. Some embodiments further comprise an amplifier connected to the first and second electrodes.

Some embodiments comprise a radiation shield that provides greater radiation shielding of junctions in the third plurality than junctions in the fourth plurality. Some embodiments comprise a heat dissipation element in thermal communication with junctions in the third plurality. Some embodiments comprise thermal insulation disposed between junctions in the third plurality and junctions in the fourth plurality.

In some embodiments junctions in the third plurality have different thermal properties than junctions in the fourth plurality. Some embodiments comprise thermal insulation disposed between junctions in the fourth plurality and ambient conditions. In some embodiments the first material and the second material provide a Seebeck effect when placed in contact with each other. Some embodiments involve a third and fourth material to provide a variability in Seebeck effects to enhance separating the penetrating radiation effect from the background temperature variation.

Some embodiments comprise a thermally insulating substrate, and wherein junctions in the third plurality are disposed on a first surface of the substrate, and junctions in the fourth plurality are disposed on a second surface, opposite the first surface, of the substrate.

In some embodiments junctions in the fourth plurality are in a vacuum. In some embodiments the heat dissipation element comprises a cold plate. In some embodiments the heat dissipation element comprises a heat sink. In some embodiments junctions in the third plurality have lower heat capacity that junctions in the fourth plurality. In some embodiments junctions in the third plurality are smaller than junctions in the fourth plurality.

In some embodiments the junctions are mounted with a substrate, and wherein junctions in the third plurality are disposed in a first region of the substrate, and junctions in the fourth plurality are disposed in a second region of the substrate, wherein the first region is distinct from the second region. In some embodiments the junctions are disposed in a two-dimensional array. In some embodiments the total number of junctions is at least 100. In some embodiments the total number of junctions is at least 1,000. In some embodiments the total number of junctions is at least 10,000. Larger numbers of junctions are also within the scope of the present invention. The number of junctions can be chosen based on fabrication considerations and desired performance, e.g., sensitivity.

In some embodiments the first material is chosen from the group consisting of bismuth, selenium, silicon, and Pbi5Ge37. In some embodiments the second material is chosen from the group consisting of bismuth, selenium, silicon, and Pbi5Ge37, excluding the first material.

The unpowered devices described herein, also described as thermopile devices, exhibit very high dynamic range, has fast time response, is small, and as a direct read of dose which will make more accurate than other technology available. The downside is that the method isn't very sensitive in a relative sense, for instance very low dose rates, within factors of many times background are not measurable. And other, large detectors have orders of magnitude more sensitivity. However, for many important uses, this technology offers significant benefits in accuracy, timing and dynamic range.

BRIEF DESCRIPTION OF THE DRAWINGS

The accompanying drawings form aspects of the specification and practice of potential embodiments of the invention. They are meant to illustrate embodiments and serve as examples. They are not meant to limit the invention. For example, intermediate sections of third Seebeck materials can be inserted between the hot and cold sides to add additional junctions and clarity in interpretation. This is not shown in the illustrations.

INDUSTRIAL APPLICABILITY AND MODES FOR CARRYING OUT THE INVENTION

The present invention concerns radiation sensors, specifically sensors that provide measurement of radiation dose and dose rate. Other commonly used radiation sensors, e.g., semiconductors, scintillators, proportional or avalanche gas sensors, thermoluminescent detectors, etc., use some sort of complex conversion to determine radiation dose. Embodiments of the present invention can use direct fundamental parameters (e.g., the Seebeck effect in a thermoelectric junction (single unit or thermopile (multiple unit)) devices. The effect can be utilized when sensing penetrating and ionizing radiation, and changing background temperatures can be accounted for in the device so that it can be an unpowered device and directly NIST-calibratable based on the fundamental physics. Embodiments of the invention can provide precision and accuracy of 1 percent or better because they can be directly related to dose without conversion or modeling of the x ray source and spectrum as required in prior art devices. Prior art devices require conversion and modeling because the energy/mass isn't directly measured. Most interaction rates have uncertainties of 5% or greater and the total uncertainty, what one gets for the additive effect of errors in the interaction parameters and modeling can degrade accuracy enough to put people at risk.

Medical applications often require precision in both measurement of ambient conditions as well as low noise, high gain amplification of the thermopile output. Short pulsed x ray sources, such as those used in most x ray machines, allow direct thermal background measurements, as well as radiation shielding near hot and cold junctions, to discriminate environmental effects from the radiation desired to be measured. Powered devices can be used or not; as the specific need for a RTD or thermopile solution requires. Depending on the source energy, differential shielding or longer leads can be used to separate the hot and cold junctions. The separation between the hot and cold junctions is important for measuring penetrating radiation; this separation helps to maximize the temperature difference seen between electrodes. Under some conditions it is enough to have different sized junctions and thermal features, however, for the best measurement of temperature rise due to the radiation it can be preferred if one junction does not get radiated at all. Hence the shielding.

Additionally, by design the materials can determine the method for obtaining and maintaining a thermal gradient across the sensor elements. By design we have a cold plate, cold junction of high heat capacity, the hot side has low heat capacity and high equivalent thermal mass (e.g. vacuum).

Another embodiment is for softer x rays (such as dental, nominally 20 keV) for this just use a through hole design with vias. We describe a number of designs for highly energetic penetrating radiation. The choice of method will depend on specific cost/benefit analysis for a specific application. However, the basic invention can work in each of the applications mentioned.

Embodiments of the present invention provide a radiation self-powered trigger as well as a monitor for dose and dose rate. It can serve as a passive signal integrator and amplitude hold capacity. This can enable low power circuitry as well as an inherently radiation-hard capability. The dose can be stored for a short time, while electronics are off, to enable survival of the signal. Normally at high doses electronics will fail or system generated EMP will affect performance. Embodiments of the invention can enable operation in normal rate, to high dose rate, and to extremely high dose rate environments as compared to most terrestrial environments.

Embodiments of the present invention provide for fabrication, assembly, operation of an electronic circuit that can operate as an accurate, compact, inexpensive, low-power, dose rate and/or dose detector for an extended range of radiation dose rate and dose for total dose, as well as separate gamma and neutron radiation. An example circuit embodiment works for both moderate total doses and for the high dose rates that are generally classified as prompt radiation events. This is a source of difficulty: the background radiation dose is 600 mrad/year and the LD 50/30 is 600 rads. The definition of 1 rad of radiation dose is 100 erg/g, also called 0.01Gy or 0.01 J/kg. An example circuit embodiment can have elements that compensate for thermal background variation in time domains that are not the same as the imposed radiation event. Because of the reliance upon basic physical parameters of the thermocouple materials the device is inherently traceable to NIST standards. Unlike other technologies, embodiments of the invention can be very radiation hard (insensitive at high doses) and the readout electronics can be near the sensor or remote from it. This can be responsive to the need or concept of operation and the sensitivities of the electronics used to read the response.

Because the sense element can be implemented as a bimetal junction, rather than a volumetric sensor such as a scintillator, the device can be small, and can be made in arrays for imaging to diagnose medical dose immediately and accurately. It can used to diagnose accidents or malicious acts as well as work in most environments where penetrating radiation is a concern or needs to be monitored.

Embodiments of the present invention provide a direct measurement of temperature divided by known heat capacity, a clean way to measure total dose. Using a thermocouple whose voltage is provided by the well-known Seebeck effect gives a temperature directly tied to a physical constant and is therefore fully traceable back to NIST standards. The sensor element itself can be unpowered and totally passive.

The Seebeck effect can be used to measure ergs/gram or radiation dose directly. It is not ordinarily used for measuring radiation for a single junction since normal radiation doses will have picovolt (pV) changes and these are much, much smaller than can be measured with current electronics. Further, in a normal junction the two ends must be at different temperatures for the Seebeck effect to be measured. With penetrating radiation when the junctions are close together then the state-of-the-art has to date not determined a way to drive a meaningful radiation-dependent temperature change at medically relevant dose rates. Further, the background thermal temperature changes will dominate the Seebeck effect, making the signal due to radiation much less than the noise measurement.

Embodiments of the present invention can overcome all of these hurdles. Embodiments use thermoelectric effects to improve performance over the current state-of-the-art and to enable measurements not currently viable. Although we show the passive designs only, resistive (or active) types are also within the scope of the invention. Such designs require control of the currents and voltages well enough to trust the output as much. The tradeoffs will be in sensitivity and cost versus accuracy.

Figure 1:
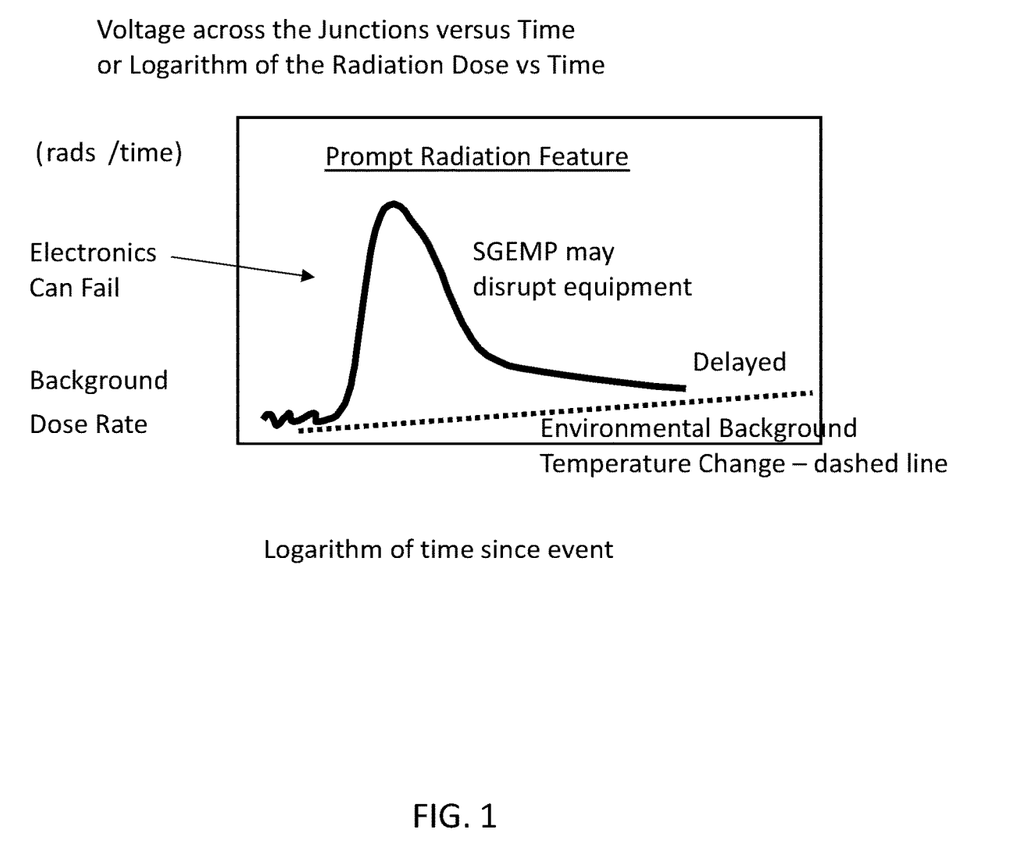
FIG. 1 is an illustration of the effect in a time domain context of something like a Fukishima event.

Embodiments combine a technique to correct for thermal drift in the background as well as signal enhancement to reduce amplification requirements over use of a single element. In addition, this can extend to unpowered sensor elements, with unpowered signal holding until main power is turned on. This feature can enable the electronics to be off while the irradiation is above normal operation levels so that the measurement can still be made. This can be important for operation through a prompt or intense radiation pulse where most electronics can fail due to radiation or SGEMP (Signal Generated Electromotive Pulse) damage. Amplification and storage of the signal can still be required. These features can be desired for space based as well as terrestrial environments. The effect in a time domain context of something like a Fukishima event is illustrated in FIG. 1. The log of the radiation dose rate is the vertical axis and the log of the time since the event is the horizontal axis. The signal initially starts at the background dose rate. After the event occurs, the signal has a sharp rise. This sharp rise can cause conventional electronics to fail and can disrupt conventional equipment. The signal then has a delayed decay portion as time passes since the event. There will be an intense burst of radiation, enough to overwhelm and potentially damage many sensors. At lower levels this same thing happens during a medical x ray and various procedures can happen quickly and some take longer. The dashed line shown represents a change in temperature background; as long as the background temperature variation is known and can be corrected for then the difference is a direct measurement of the penetrating radiation dose because the inverse ratio of the Seebeck Coefficient divided by the heat capacity times the voltage is the ergs/g. That is the direct measurement of the dose. The effect shown in the figure also corresponds to a CAT scan and a signal at a distance from a terrorist nuclear event as well.

Traditional high dose sensors use active circuit measurements and charge depletion (semiconductors) for dose measurements. They saturate at high doses and need complex calibration. Variants of this are true for most sensors currently in use, including scintillators, Geiger-Mueller tubes (gas avalanche) and semiconductor sensors.

Using the inherent voltage drop across a thermocouple means that the measured response is due to the inherent dissimilar response of the metals to temperature providing known thermoelectric effect (the Seebeck effect). This means that the sensor is inherently calibrated and unpowered and the effect is determined by the basic physical parameters of the materials without some external gain or conversion required. A direct measurement of temperature divided by known specific heat capacity (e.g. ergs/kg-K) is a clean way to measure total dose which is defined in terms of ergs/kg or ergs/gram. Using a thermocouple whose voltage is provided by the well-known Seebeck effect gives a temperature directly tied to a physical constant and is therefore fully traceable back to NIST standards. The dose can be found according to dose=dt=$C_p/S_b$*dV, where dose is the dose in rads, $C_p$ is the specific heat capacity in ergs/K-kg, the Seebeck coefficient, $S_b$, is the voltage change, dV, per unit temperature (uV/K). The trick to accuracy is then knowing the heat capacity, the Seebeck coefficient and the change in voltage. The two materials constants and the change in voltage are known and can be measured accurately.

A comment on units. We use various units throughout this specification and attempt to stay with commonly used ones. We assume the reader is well enough versed in the fields to be able to convert units.

This system can provide a 'gold standard' measurement of moderate radiation dose and dose rates, meaning NIST-level documented dose and dose rate measurements in a low power package. Two or more differing type thermocouples (for example R and K-type; others are also useful) can be placed in a thermally-insulated package and background signal for environmental temperature adjustments subtracted. The thermocouples offer differing differential sensitivities and heat capacities. In the presence of a radiation field the responses will differ and the subtracted signal in the presence of a radiation signal reflects the heating from radiation alone over the time period of the thermal response of the unit. High gain amplification can be used to see the small heating effects from radiation in most cases. Because dose is defined as energy per gram the temperature rise directly determines dose.

If the dose rates are too high for direct digital manipulation, e.g., the processing electronics will be disabled by radiation at that dose rate, then a passive sample and hold circuit, such as those known in the art can be used so that the needed signal recorder can be turned off during the event (this is routinely done with a silicon rectifier circuit) and restored once the dose is reduced to acceptable levels. When the digital electronics can be turned on the signal can be captured and exfiltrated via wired or wireless means for complete processing.

Changes in environmental temperature, normal variation in temperature through the course of a minute, hour day or year can be very large compared to the dose of radiation that one needs to measure and embodiments of the invention provide, using a second thermopile array of differential performance as described in the equations below or by use of another thermal sensor, to subtract or otherwise correct for these variations.

Embodiments can use two or more dissimilar units to correct for environmental variations in temperature allowing for correction of normal background temperature drift and separating the heating elements associated with radiation.

Figure 2:
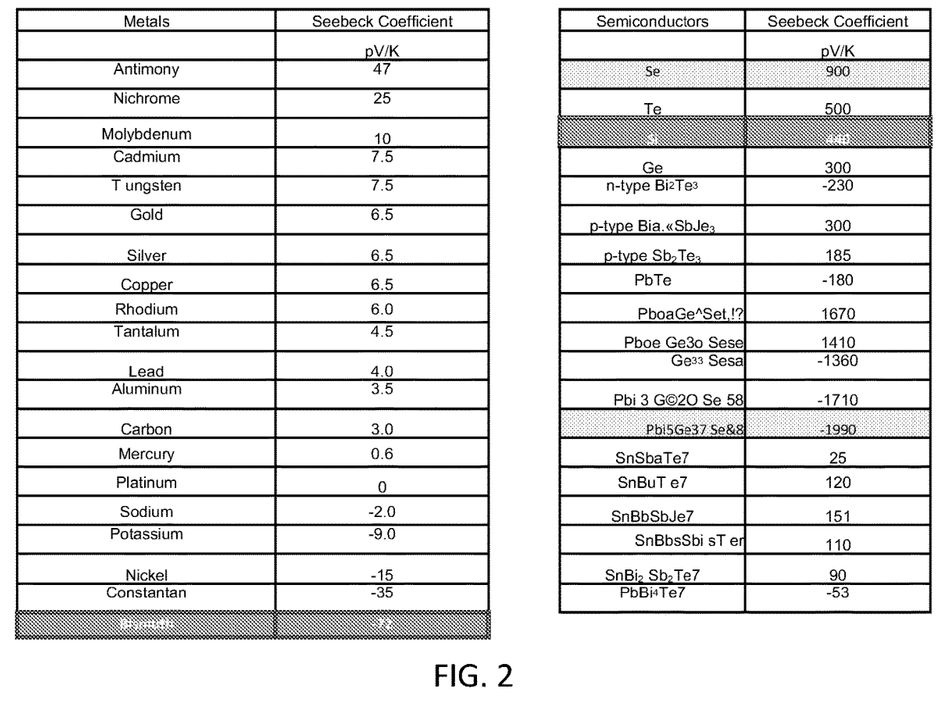
FIG. 2 illustrates some basic physical parameters relevant to the present invention. (from omega.com).
Figure 3:
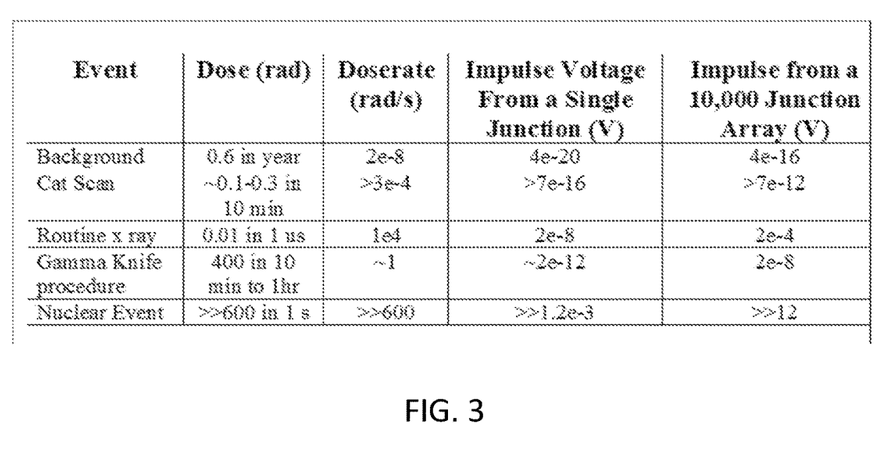
FIG. 3. Radiation events of interest compared to the total Dose and Dose Rates as well as measurement ranges for device operation in terms of impulse voltage from a single junction versus a 10,000-junction thermocouple (a multiple junction thermocouple is defined as a thermopile).

The voltage drop or EMF (electromotive force) across bimetal junctions is well known. See FIG. 2, taken from https://www.iomega.com/techref/pdf/z016.pdf, for an overview of such materials. The shaded areas represent two examples of good choices for paired thermocouple materials. A simple model for a given bimetal junction has the voltage drop, or relative Seebeck effect across the junction, expressed as:

$$\Delta V_i(t) = S_i(T) * \Delta T(t)$$

where the voltage drop of the ith bimetal junction as a function of time (t), $V_i(t)$, is the product of the metal's Seebeck effect, Si[V/K] and the temperature. See FIG. 2 for some physical parameters of materials relevant to this description. There is a tradeoff between the number of thermocouple junctions and amplifier gain and the analogue to digital (A/D) converter that will determine how useful these devices are for any application. We give some simple examples in FIG. 3. Note how with an A/D converter, amplifier combination that gives a sensitivity over $10^{-9}$ V (difficult but achievable; greater than $10^{12}$V has been done). The device will give the ability to measure doses for routine x rays, gamma knife, and nuclear events. Variations on this design to enable more applications will be apparent to those skilled in the art.

The temperature can be considered as the sum of an environmental component and a radiation-induced temperature change or $T(t)=T_e(t)+T_{rad}(t)$. The environmental temperature can be made to vary slowly in time by insulation or other design characteristic and $T_{rad,i}(t)$ due to the radiation is related to the dose [cGy or rads] and is given by:

$$T_{rad}(t, K) = \frac{R(t)}{C_i} * 2.39 \times 10 - 8 \text{ cal/erg}$$

where R(t) is the dose and Ci is the heat capacity of the ith thermocouple [cal/g-K]. $T_e$ (instantaneous device temperature or environmental temperature) can also be solved simultaneously as this is a system of i-equations and i-unknowns. This provides a powerful technique for both penetrating radiation and thermal radiation in low power devices. Note this is a very small number, for instance, a single junction of C=0.1 cal/g-K will have a temperature variation of 2.4e−7K. To get a 1 rad step change with a 10 uV/K junction and no thermal diffusion effects can require a 2.4e-12 V (or 2.4 pV) measurement.

To put this in perspective see FIG. 3. FIG. 3 relates events that a radiation sensor might need to respond to and it sets the engineering parameters, such as number of junctions, for aspects of device design. It is relatively easy to measure 1e-4 Volts and with some effort and expense to measure 1e-12 V (1 pV can be measured with effort). This means, in this estimate, that a 10, 000 element array is a feasible device to accurately measure the dose from a medical x ray with a nominal 200 uV signal. Measurement of gamma knife irradiations can benefit from more junctions, more signal amplification/noise reduction, or a combination thereof. Systems such as those used with patch clamps can directly measure picoamps.

There are also efforts to develop x-ray sources bright enough to deliver a traditional x ray in ~100 ns. With this type of x-ray source from a pinch or dense plasma focus, the equivalent signal is 1 mV or greater.

Instantaneous measurements of damaging doses to tissue can be made and imaged in time to shut down critical equipment prior to someone being overdosed or damaged. This type of circuit can prevent medical tragedies.

Note that any device will be affected by thermal diffusion. Those skilled in the art can model and account for those effects in their usage. The figures illustrate different ways to account for this and to design for short pulses or long ones, long being >1 second and short of order of nanoseconds. Pulses shorter than milliseconds might not need a large correction for thermal diffusion away from the sensing element.

Figure 4A:
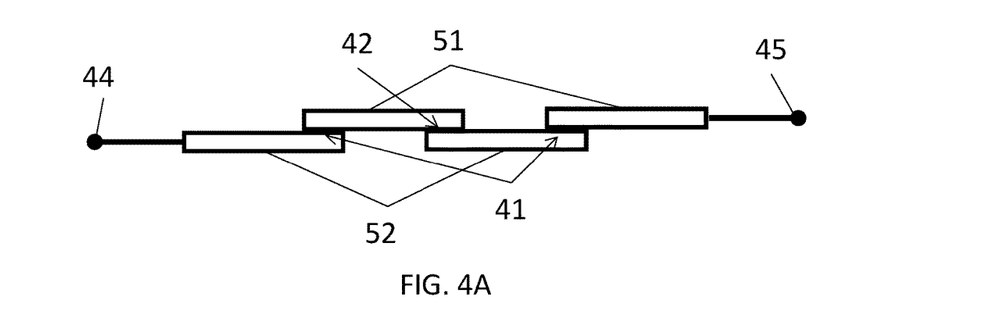
FIG. 4A illustrates a basic multi-junction thermopile concept.

Using more than one junction type allows embodiments to measure the thermal and radiation effects differentially in more than one type of junction. Since the heat capacities are different the equation governing the voltage measurements can be parsed to determine the environmental temperature change as separate from that due to the penetrating radiation. FIG. 4A shows an example simple thermocouple and pile configuration. A first material 51 and second material 52 together form a plurality of thermocouple, one in each region of overlap 41, 42. The thermocouples can be configured to experience different temperatures after exposure to radiation, as examples by placing thermal insulation between them; by placing alternate thermocouples in communication with a cold plate, heat sink, or other thermal management system; by shielding alternate thermocouples from incident radiation; by making the thermocouples such that alternate thermocouples have different heat capacity or conductivity, or any combination of the previous.

The series of thermocouples are in communication with thermocouple measuring junctions 44, 45. The junctions are typically in communication with a circuit, comprising an amplifier, and an analog-to-digital converter (A/D) and the input and output electrodes complete the circuit. The voltage output of the A/D converter is read by an oscilloscope, chart recorder or electronic analogue as a storage medium. The functionality of all of these can be included on a single chip or Floating-Point Gate Array (FPGA). Labjack and National Instrument equipment are examples of suitable equipment, and there are many options known to those skilled in the art. Those skilled in the art will also appreciate implementations using custom embedded circuitry.

The present invention is particularly useful in the arena of nuclear forensics or situations where the primary electronics may saturate, will not work, need to be reset or for other reasons cannot be trusted. We use the relatively short turn on time of a Cortex-M0 processor and circuit digitization circuit and we connect the output of a thermopile array to a parallel set of resistive-capacitive circuits to store the output current in passively time-filtered circuit and then read the voltage, after the circuit has powered on, in order to provide a few data points (i.e. dose at time below the filter cutoffs of (for example 1 us, 100 us, 1 ms, 10 ms). In this case the entire circuit can be powered down or at very low power, until the thermopile output (e.g., 0.1V) is used to trigger the processing elements of the circuit. SCR (silicon rectifier circuits) have been used (see Aquilagroup.com) to power down sensitive circuitry and after a set period of time then power it up. With the use of the thermopile as a passive voltage generator the circuit can be off for long periods and then triggered to turn on the read process allowing lower power use.

Embodiments of the invention use an array of thermally activated elements to add a small amount of voltage with each consecutive junction. The present invention is to be able to employ them with penetrating radiation and apply them to the many applications already discussed. That means fabricating large arrays, e.g., 100 to 1,000,000 or even more junctions, including the methods described for background correction from environmental changes and to provide a temperature difference. We use designs (large and small electrode, high and low conductivity materials, high and low heat capacity materials) such as those shown in the figures, to extend the temperature differences between the hot and cold electrodes, and we can use shielding and distance to physically separate the penetrating and ionizing radiation from heating both the hot and cold electrodes.

Figure 4B:
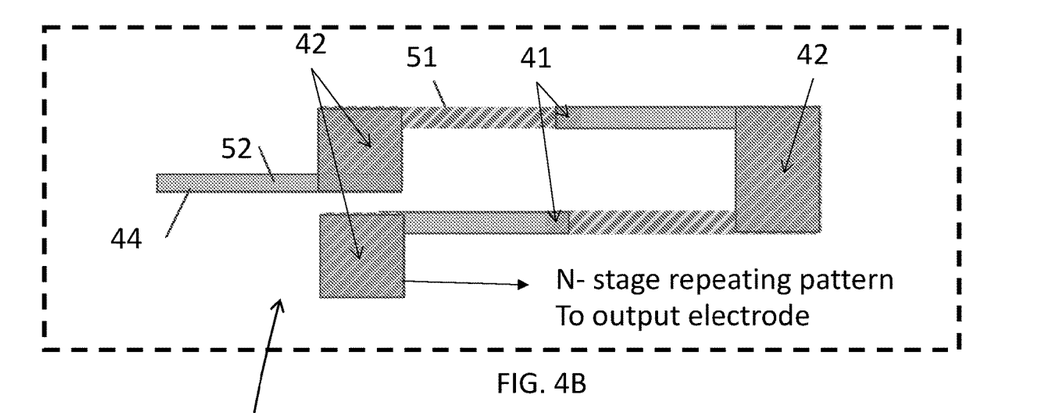
FIG. 4B illustrates a configuration for a thermopile radiation sensor based on a design for a thermopile to be fabricated using lithographic processes on a surface.

FIG. 4B illustrates an example surface fabricated system. An input electrode 44 is connected to a second material 52, which forms junctions with a first material 51. The materials overlap in the regions indicated, with the junction formed by the materials as they touch in the area of overlap. A cold junction 41 is small with less thermal mass. Hot junctions 42 are large with more thermal mass as shown in FIG. 4B

Figure 4C:
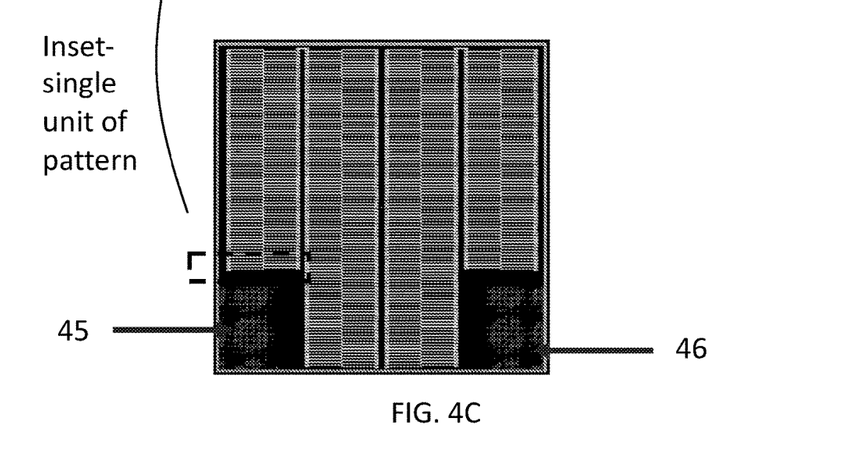
FIG. 4C shows a flat embodiment for a thermopile with 100's of units.
Figure 5:
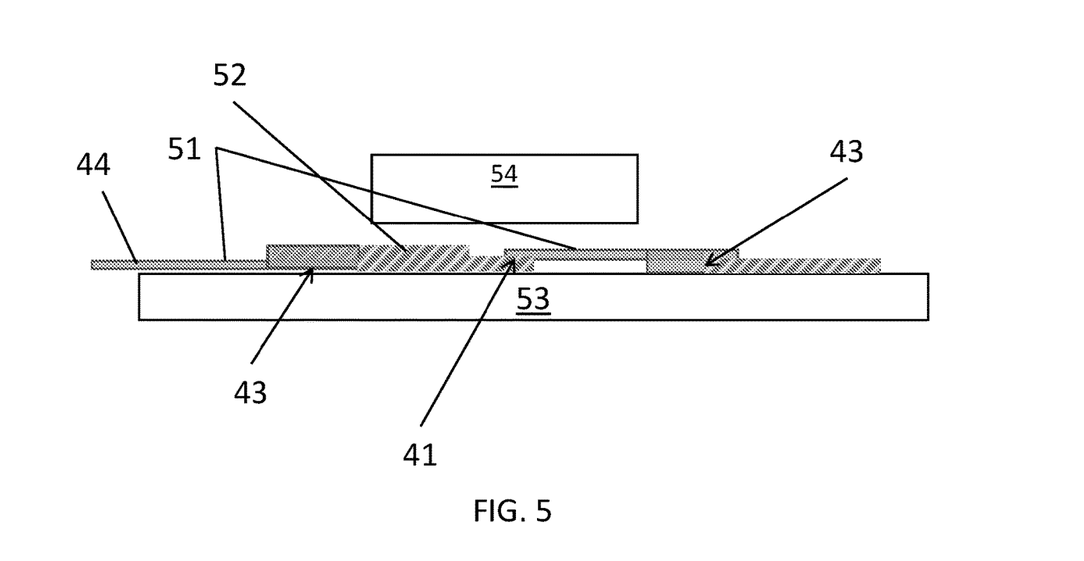
FIG. 5 provides schematic illustrations of example embodiments of pile configurations constructed in a through-hole via configuration. The hot and cold junctions can be separated so that the either the penetrating radiation illuminates each junction differently or each junction retains heat differently.

FIG. 4c shows many of the junctions made in series to raise the relatively small temperature rise per junction to a quantifiable level. The device of FIG. 4C can be made by repeating the device of FIG. 4b. The example in the figure is a 812 unit pattern. The junctions are connected in electrical series between an input electrode pad 45 and an output electrode pad 46. When we build two roughly identical systems (for instance using Materials 51 and 52) but of different materials, and with differing responses, by design, to the thermal background we then can separate the background result and obtain the penetrating or ionizing radiation component of the total temperature. This complexity isn't always needed however it can help bring the signal from penetrating radiation above the thermal background noise FIG. 5 illustrates heat transfer aspects of embodiments of the invention. The first 51 and second 52 materials can be used to form thermocouples on one or both sides of a thermal resistance material substrate 53. The materials overlap such that there is a junction in each region where the materials overlap. Heat flux, q", exits the junctions. In operation, the larger hot junctions 43 have greater heat capacity than the smaller cold junctions 41, and, as the junctions heat or cool, the resulting temperature differential will cause voltage differential between the ends of the array of thermocouples. This is quite reasonable for photons below nominally 200 keV. This is adequate for chest x rays and lower energies. The entire system can be quite small. The device shown can be repeated for multiple stages to an output electrode (not shown). A radiation-shielding material can optionally be disposed such that it blocks the cold junctions from incident radiation, further contributing to the temperature differential.

Note that if both junctions are at the same temperature then there is no Seebeck effect or voltage to measure. These examples show embodiments for each case—large separation whereby the radiation field at the hot and junctions are different or where dissimilar materials are used to enhance cooling, or high heat capacity on one end and heat capture or low heat capacity at the other.

Figure 6:
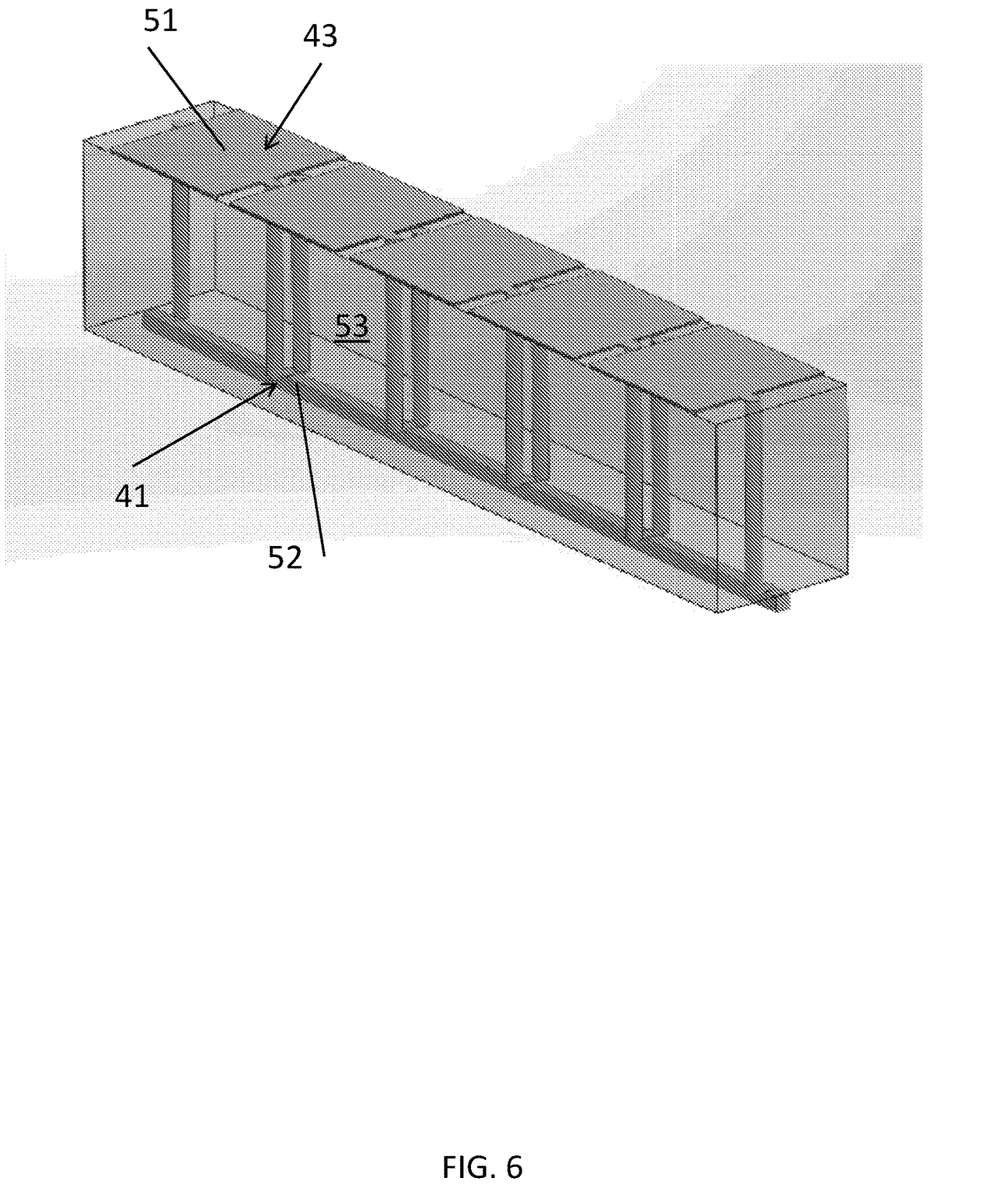
FIG. 6 is a perspective view and FIG. 6A is a sectional view of a schematic illustration of an example embodiment of a surface patterned array of thermocouple junctions with cold junction located in the center. The cold junctions are shielded from the radiation with a high Z, high density plate such as tungsten to reduce the dose at the cold junctions enhancing the response from the penetrating radiation over that which can be achieved by material choice and geometry alone. This can also be implemented in the geometry of FIG. 4.
Figure 7:
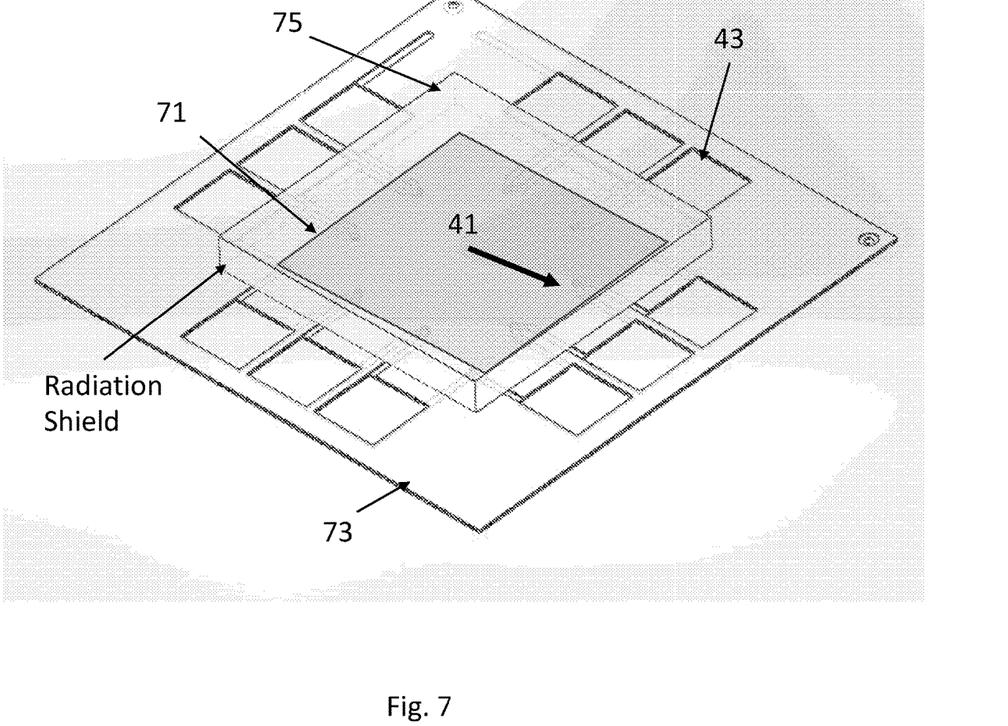
FIG. 7 is a schematic representation of a passive element thermopile design for compact measurement of penetrating radiation dose using the through-hole via design.
Figure 8:
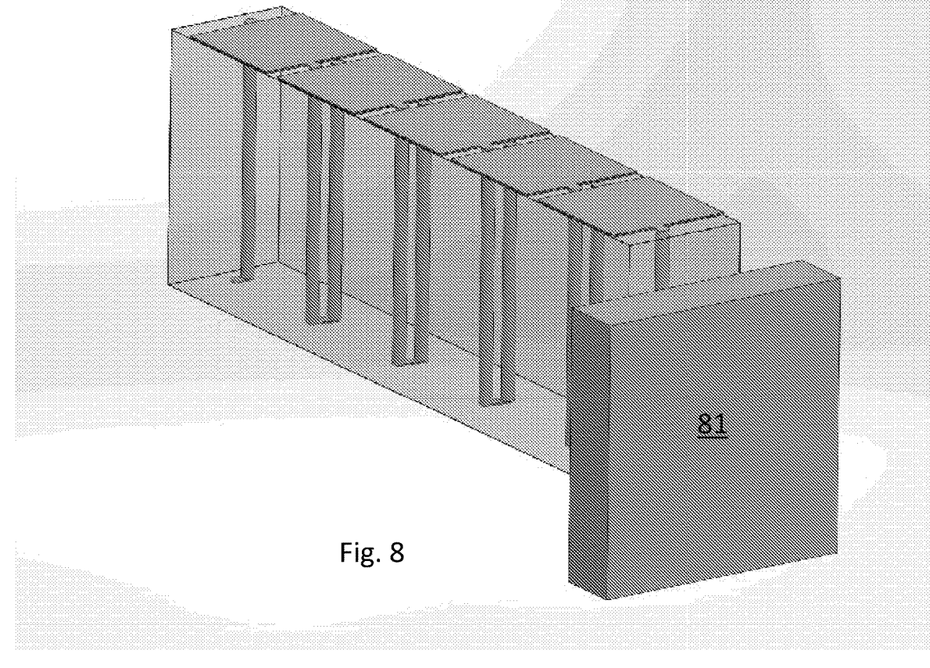
FIG. 8 is a schematic of either of the thermopile layouts which could be configured into a ring for assistance to doctors or medical personnel performing procedures such as fluoroscopy where their hands could be in the radiation field.

The problem of a very low signal in a single junction can be overcome by placing many junctions in series, see FIG. 4C and FIGS. 6, 7, 8, for various fabrication styles. However, the thermal effects should be compensated for in ways that cannot be done as is done in current thin film or MEMs systems with multiple junctions. FIGS. 6-8 provide schematic illustrations of example embodiments that can generate adequate signal and correct for the effects of the penetrating radiation.

Figure 6A:
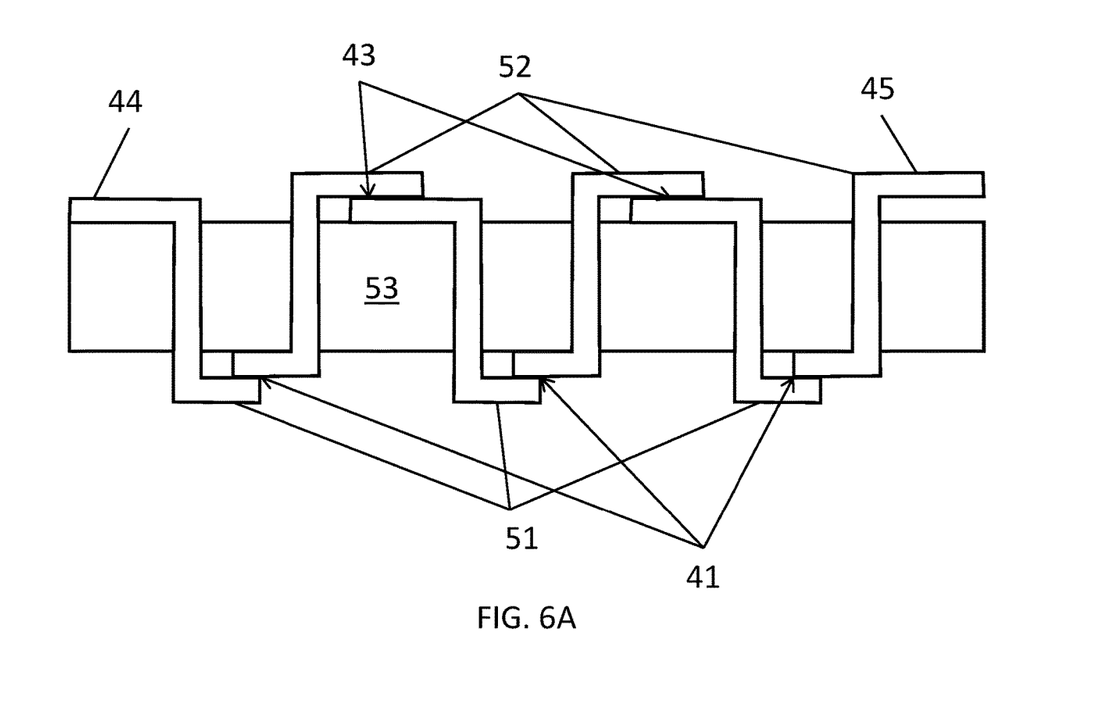

FIGS. 4B and FIG. 4C illustrate a surface plating/coating process for making a massive array of thermocouples. FIG. 6A (schematic, in section) and FIG. 6 (perspective) illustrate an example embodiment using through-hole via fabrication that can provide generate adequate signal and correct for the effects of the penetrating radiation by using controlled heat capacities and junction parameters on 'hot' and 'cold' sides to develop voltage differences with penetrating radiation. The substrate 53 comprises an insulator with holes that have been filled with copper or two materials 51, 52. In FIG. 6A the vertical portions of the elements made of the two materials correspond to vias in the substrate. If the vias are filled with coper or another conducive material, then the material 51 or 52 is disposed at the ends of the copper-filled vias. The substrate 53 can be a temperature-controlled surface such as a thermoelectric chiller which is electrically separated from the other elements of the sensor. The elements are connected in electrical series until the first 44 and last electrodes 45 in the series layout. The first and last electrodes are then coupled to the read electronics (not shown). The read electronics will comprise a filter set if needed, amplifiers, impedance matching circuits, if needed, and then the analogue to digital readout and storage. After the storage will come processing and exfiltration of the data to its more final analysis stage. The arrangement shown can comprise a single row or column of an array of sensors, connected overall in series. The number of junctions in each row or column can be more or less than the number shown in the figure. Those skilled in the art will appreciate other geometric arrangements of the elements that still yield the alternative hot and cold junctions.

To facilitate the desired temperature differential, a radiation shield can be deployed to reduce the radiation reaching the cold junctions. The hot junctions can be placed in communication with an insulator, e.g., a vacuum. The cold junctions can be placed in communication with a cold plate, heat sink, or other heat dissipation feature. The hot junctions can be made larger, as shown in the figure, to provide greater heat capacity than the cold junctions. Combinations of these techniques can also be used.

The embodiment of FIG. 7 comprises a device fabricated like that in FIG. 4 with a different layout. A cold plate 71 can be placed in communication with the cold junctions 41, for example on top of or underneath the region containing the cold junctions. underneath. The cold plate 71 is in contact with the thermocouple materials on a first side of a thermal resistance material. The other side of the thermal resistance material is in a vacuum, such that the hot junctions cannot readily dissipate heat due to incident radiation. The junctions are mounted on a substrate 73 that is thermally conductive but electrically insulating. Above (in the figure, can also be below or surrounding) the cold junctions is a radiation shield, 75. The thermocouples are disposed on the surface of the substrate such that the cold junctions are near each other, facilitating efficient heat communication with the cold plate or other heat dissipation element. This enhances the temperature differences from the hot junctions to cold junctions based on the heat capacity differences in the materials.

Such arrays can also be stacked on top of each other, for example two arrays can be disposed, one on each side of the cold plate, increasing (e.g., doubling) the number of junctions contributing to the measurement. The thickness and the properties of the various materials can be selected so that the temperature response is appropriate for the intended dose rate and application, allowing the entire unit to be completely passive (requiring no active cooling or heating). The embodiment is sensitive to radiation from any direction. This embodiment can be implemented as a small device, and can be manufactured with traditional machining and assembly methods or using MEMs and microfabrication techniques. The thinner (e.g., 10×) thermocouple junctions, near the cold side can be made so as to rapidly equilibrate with the cold source. The thicker junctions on the vacuum side can retain heat longer to extend the time response. A single junction will provide good signal to noise in a 10M Rad/s dose environments. 10^4 junctions will work well in 1e3 rad/s environments or greater. The designs of both FIG. 4 and FIG. 7 can be reconfigured to make the distance between the hot and cold junctions many centimeters. Because wafers are made in 4 inch to 12 inch diameter, variations of either design (flat or through-hole) can made with adequate separation to provide shielding useful to photon energies above 10 MeV or other penetrating radiation. For example, a wafer with many cm distance between the cold and hot junctions can be made and shielding provided. These examples can be useful in high energy physics, inertial confinement physics and pulsed power environments. This distance can provide shielding to extend the design into the many MeV of photon energy and for extremely penetrating radiation and this is useful for nuclear forensics, for laboratory work and for basic science studies with laser, pulsed power or beams.

The embodiment of FIG. 8 comprises a device like that in FIG. 6A and FIG. 6B. in this example embodiment, designed for more penetrating radiation and/or higher level of discrimination against environmental effects, a radiation shield 81 is added. The shield can comprise a Hi-Z, high density material such as tungsten, and provide shielding for the cold junctions. This embodiment can also be suitable for machine monitoring (medical x ray or simulation sciences, laboratory experiments, etc.) measurement of penetrating radiation dose. This embodiment can be implemented as a small device and can be manufactured with traditional machining and assembly methods or using MEMs and microfabrication techniques. The example shown can also comprise a single row or column in an array of junctions, connected in series for high sensitivity. Hydrogenous or other low atomic number materials can also be used for neutron detection.

A single junction can provide good signal to noise in a 10M Rad/s dose environment. The specific usage can define the number of junctions required and the number can be varied to generate high dynamic range.

Figure 9:
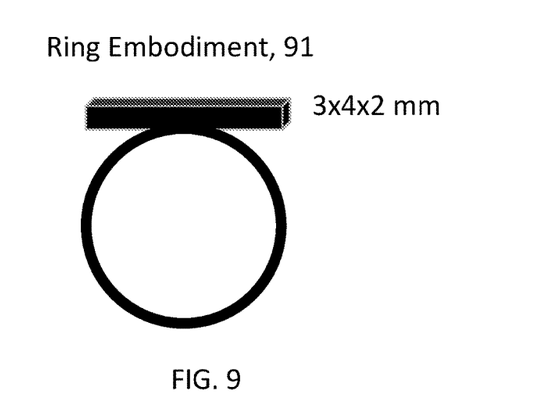
FIG. 9 is a schematic illustration of an example embodiment.

FIG. 9 is an illustration of an example embodiment and packaging for ring scale unit. This type of unit can be suitable for medical dose of record using thermopile and low gain amplifier to Bluetooth or other transmitter. An example is that a 40×40 array of thermocouples can fit on a 5×4×1 mm device and a small battery can provide power to a transmitter and amplifier (or a thin power line) to exfiltrate the data. In a two-sided configuration with parameters as described herein, this embodiment can hold 3,200 junctions making the ring adequate for time-resolved dose measurements below 200 keV in photon energy. 12,000 junctions can be feasible. A simple battery system can provide 3 hours of operation with currently available electronics. The technology is suitable for medical dose of record because the sensor itself is tied to the fundamental Seebeck phenomenon and the entire electrical path can be calibrated at any time with the addition of a VCSEL (or other light source) or thermal heater built into a chip. In this way the entire system can be calibrated and tied to a physical phenomenon. This method of calibration results in better calibration than those of TLD (thermoluminescent detectors) or OSL (Optically Stimulated Luminescence) which is another contender.

FIG. 9 is an illustration of an example embodiment and packaging for ring scale unit. An example ring 91 can be 3×4 mm×2 mm and contain a transmitter and battery. The ring 91 is mounted with a thermoelectric chiller 92. The ring can be worn by medical professionals, emergency responders, etc. This type of unit can be suitable for medical dose of record using thermopile and low gain amplifier to Bluetooth or other transmitter. The technology is suitable for medical dose of record because the sensor itself is tied to the fundamental Seebeck phenomenon and the entire electrical path can be calibrated at any time with the addition of a VCSEL (or other light source) or thermal heater built into a chip. In this way the entire system can be calibrated and tied to a physical phenomenon.

By tiling, making an array of sensors (not just junctions), similar elements to those in the ring, a sheet of many of the sense elements can make a flexible imaging array. In this manner the devices can be used to image radiation dose in time with the same extraordinary accuracy. This type of unit is suitable for medical dose of record in an imaging format.

The example embodiments described herein can be used without assisted voltage amplification. Even with 10,000 junctions the signal level can be small. However, it can be boosted, for example a commercial amplifier such as the Alligator technologies USB-PBP-S1 and a Lab Jack T7 can be used to successfully amplify a single junction E and T-type to useful signals with 100× to 10,000× gain. This gain resulted in thermal level DC voltages that are difficult to compensate. The thermopile design will fix this problem. Thermal noise background in the amplification stage was the greatest noise problem. By using these serial junctions with lower gain amplifiers that have larger gates or HBT electronics which are inherently less sensitive to radiation we can employ gain to boost the signals into the volt range and suppress the thermal background as well as parasitic defects caused by radiation in the active analog electronics, with capacitive blocking and other techniques.

The direct or amplified voltage of the thermopile can be used to turn on, or trigger, downline digital or analog circuitry using passive or active elements reducing power loads and radiation damage in high environments simply by having the circuitry off during the highest points of the radiation pulse.

The sensing elements can be collocated with processing electronics or be physically separate to provide a reduced radiation signal at the electronics; a sample and hold can be placed on the signal providing additional flexibility in the concept of operation of the assembled device (e.g. for battlefield vs operating theater, etc.).

For one application, soldiers might get exposed to nuclear effects from nuclear weapons, accidents or terrorist events and the need is for tools to provide triage information. Therefore, the circuit should provide a useful readout and survive ~10 Mrads/minute (for instance 1 Mrad/min*1 ms-burst=17 rads) as well as provide an accurate reading of the dose. Embodiments allow use of a simple analog circuit as the sensing circuit coupled with a circuit that is somewhat radiation hardened to provide real-time accurate readout in the field. This addresses two problems: (1) a sensor useful in the biological regime and (2) a readout which is insensitive at the doses and dose rates required. Another common need for such devices is in medical situations, both to protect and monitor the staff as well as patients both during and after procedures.

With low energy radiation the effect is essentially a surface effect, hence the use of resistive and thermocouple arrays for IR radiation. The present invention is also suitable for high energy and penetrating radiation. This complicates the use of these sensor elements because in accurate/normal use the Seebeck effect requires a cold junction or reference temperature at one end of the junction wires. For some circumstances, such as when a known time marker or trigger can be provided, such as for a short burst of radiation where long cables (long may be a few cm and they can be built into a wafer) can be used to move the junction away from the radiation source, a simple background subtraction technique can be used to correct for thermal drift. For other usages the sensor and the reference back plate will be seeing the same radiation field; we manage this by using a backplate of a material with a very different thermal heat capacity.

Because the sensor is meant to be used for intense burst of radiation non-linear effects from changes in background are not needed for many measurements. However, for the most accurate measurements corrections for both environmental changes in temperature and relative humidity can be made with high accuracy. There are many gauges on the market with the needed accuracy, one example is the EI-1050 sold by Labjack, baseline temperature and humidity can be modified and simple linear or higher order fits can be used to adjust for background changes while the variation in signal from the background changes can be corrected. A simple example of this is to obtain an equivalent dose measurement curve at multiple temperatures $D_B(T,t)$, where $D_B$ is the inferred dose, t is the time, and T is the temperature with no external dose provided. Then $D_T(\phi,t)=D(\phi)+D_B(T)-D_B(T_0)$. $T_0$ is the reference temperature, $D_T(\phi,T)$ is the temperature corrected dose at a flux corrected for background temperature changes, $\phi$ is the flux, and $D(\phi)$ is the inferred time dependent dose without a temperature correction. The same process can be used to correct for any changes due to relative humidity.

The present invention has been described in connection with various example embodiments. It will be understood that the above descriptions are merely illustrative of the applications of the principles of the present invention, the scope of which is to be determined by the claims viewed in light of the specification. Other variants and modifications of the invention will be apparent to those skilled in the art.

I claim:

1. An apparatus for the measurement of penetrating or ionizing radiation incident along a radiation axis, comprising:
   (a) a first plurality of elements comprising a first material; and
   (b) a second plurality of elements comprising a second material;
   (c) the first plurality of elements and second plurality of elements being configured to form a first plurality of junctions and second plurality of junctions, connected in series comprising alternating junctions from the first plurality of junctions and the second plurality of junctions to define a series of junctions; a first junction in the series of junctions in electrical communication with a first electrode, and a last junction in the series of junctions in electrical communication with a second electrode;
   (d) junctions in the first plurality of junctions having a thermal response to penetrating or ionizing incident radiation different than a thermal response of junctions in the second plurality of junctions to penetrating or ionizing incident radiation based on at least one of (1) a distance between the first plurality of junctions and the second plurality of junctions and relative to a direction of the penetrating or ionizing incident radiation, or (2) differential shielding associated with the first plurality of junctions and the second plurality of junctions.

2. The apparatus of claim 1, further comprising an amplifier connected to the first electrode and the second electrode.

3. The apparatus of claim 1, further comprising a radiation shield that, during operation, provides the differential shielding by greater radiation shielding of junctions in the first plurality of junctions than junctions in the second plurality of junctions.

4. The apparatus of claim 1, wherein junctions in the first plurality of junctions have different thermal properties than junctions in the second plurality of junctions.

5. The apparatus of claim 1, wherein the first material and the second material provide a Seebeck effect when placed in contact with each other.

6. The apparatus of claim 1, further comprising
a thermally insulating substrate,
junctions in first plurality of junctions are disposed on a first surface of the thermally and radiation insulating substrate, and
junctions in the second plurality of junctions are disposed on a second surface, opposite the first surface, of the thermally and radiation insulating substrate.

7. The apparatus of claim 1, wherein junctions in the second plurality of junctions are in a vacuum.

8. The apparatus of claim 1, wherein junctions in the first plurality of junctions have lower heat capacity than junctions in the second plurality of junctions.

9. The apparatus of claim 8, wherein junctions in the first plurality of junctions are smaller than junctions in the second plurality of junctions.

10. The apparatus of claim 1, wherein a total number of junctions in the first plurality of junctions nd the second plurality of junctions is at least 1,000.

11. The apparatus of claim 1, wherein a total number of junctions in the first plurality of junctions and the second plurality of junctions is at least 10,000.

12. The apparatus of claim 1, wherein the first material is chosen from the group consisting of bismuth, selenium, germanium, silicon, and Pbi5Ge37.

13. The apparatus of claim 12, wherein the second material is chosen from the group consisting of bismuth, selenium, silicon, germanium and Pbi5Ge37.

14. The apparatus of claim 3, further comprising thermal insulation disposed between junctions in the first plurality of junctions and junctions in the second plurality of junctions.

15. The apparatus of claim 1, further comprising thermal insulation disposed between junctions in the first plurality of junctions and junctions in the second plurality of junctions.

16. The apparatus of claim 1, wherein the first plurality of junctions and the second plurality of junctions collectively are disposed in a three-dimensional array.

17. The apparatus of claim 1, wherein;
the first plurality of junctions are disposed along a first junction axis substantially parallel to the radiation axis, the second plurality of junctions are disposed along a second junction axis substantially parallel to the radiation axis, the first junction axis separated from the second junction axis by distance that is perpendicular to the radiation axis; and
the apparatus further comprising a radiation shield that, during operation, is disposed between the second plurality of junctions and the penetrating or ionizing incident radiation and not between the first plurality of junctions and the penetrating or ionizing incident radiation such that the radiation shield provides the differential shielding by preventing radiation from reaching the second plurality of junctions and not preventing radiation from reaching the first plurality of junctions.

18. The apparatus of claim 1, wherein;
the first plurality of junctions is separated from the second plurality of junctions by the distance that is measured parallel to the radiation axis; and
the apparatus further comprising a material disposed between the first plurality of junctions and the second plurality of junctions,
during operation, the distance and the material attenuating penetrating or ionizing radiation such that the penetrating or ionizing radiation impinging on the first plurality of junctions is different than the penetrating or ionizing radiation impinging on the second plurality of junctions.

19. The apparatus of claim 1, wherein;
the first plurality of junctions and the second plurality of junctions are disposed in a plane, and
the apparatus further comprising a shield disposed such that, during operation, the shield blocks the penetrating or ionizing radiation from reaching the second plurality of junctions and does not block the penetrating or ionizing radiation from reaching the first plurality of junctions.

20. A method of measuring a dose of a pulse penetrating or ionizing radiation, the method comprising:
(a) providing an apparatus as in claim 1;
(b) subjecting the apparatus to the pulse of the penetrating or ionizing radiation that irradiates an entire volume of the first plurality of junctions;
(c) measuring a voltage differential between junctions in the first plurality of junctions and junctions in the second plurality of junctions at a time less than an thermal conductivity time between junctions in the first plurality of junctions and junctions in the second plurality of junctions; and
(d) determining the dose of the pulse of penetrating or ionizing radiation from the voltage differential and the Seebeck coefficient of the first material and the second material.

* * * * *